United States Patent [19]

Nash et al.

[11] Patent Number: 4,811,735
[45] Date of Patent: Mar. 14, 1989

[54] STONE DESTROYING CATHETER AND METHOD OF USE

[75] Inventors: John Nash, Downingtown; Mark Michels, Glen Mills, both of Pa.

[73] Assignee: Kensey Nash Corporation, Exton, Pa.

[21] Appl. No.: 79,610

[22] Filed: Jul. 30, 1987

[51] Int. Cl.$^4$ .............................................. A61B 17/00
[52] U.S. Cl. ..................... 128/305; 128/328; 604/22
[58] Field of Search ............... 128/328, 305; 604/22

[56] References Cited

U.S. PATENT DOCUMENTS

| | | | |
|---|---|---|---|
| 3,831,585 | 8/1974 | Brondy | 128/328 |
| 4,002,169 | 1/1977 | Cupler | 604/22 |
| 4,509,517 | 4/1985 | Zibelin | 128/328 |
| 4,611,594 | 9/1986 | Grayhack et al. | 128/328 |
| 4,679,558 | 7/1987 | Kensey et al. | 128/328 |
| 4,712,547 | 12/1987 | Bonnet | 128/305 |
| 4,739,760 | 4/1988 | Chin et al. | 604/22 |

FOREIGN PATENT DOCUMENTS

| | | | |
|---|---|---|---|
| 2933266 | 5/1981 | Fed. Rep. of Germany | 128/328 |
| 2945237 | 5/1981 | Fed. Rep. of Germany | 128/328 |
| 3522649 | 1/1986 | Fed. Rep. of Germany | 128/328 |

Primary Examiner—Albert W. Davis, Jr.
Attorney, Agent, or Firm—Caesar, Rivise, Bernstein, Cohen & Pokotilow, Ltd.

[57] ABSTRACT

Apparatus for disintegrating or otherwise destroying a stone, such as a gallstone, within the body of a living being. The apparatus comprises a small diameter catheter having a longitudinal axis and a working head located at the distal end thereof. The catheter is capable of being located at any position within the body so that the working head is adjacent the stone. The working head is arranged to be rotated at a high speed about the longitudinal axis of the catheter. The working head comprises at least one bladed member having an impacting surface thereon. The bladed member is arranged to move from a retracted position wherein its impacting surface is located adjacent the periphery of the catheter to an extended position wherein the impacting surface extend substantially beyond the periphery of the catheter when the working head is rotated. The impacting surface is arranged so that when it rotates in the extended position, it impacts the stone to disintegrate or otherwise destroy the stone. A shroud is provided about the distal end of the catheter to aid in directing the stone to the rotating blade while also projecting adjacent body tissue from being engaged by the rotating blade. The rotating blade creates a vortex tending to pull the stone into the blade.

33 Claims, 3 Drawing Sheets

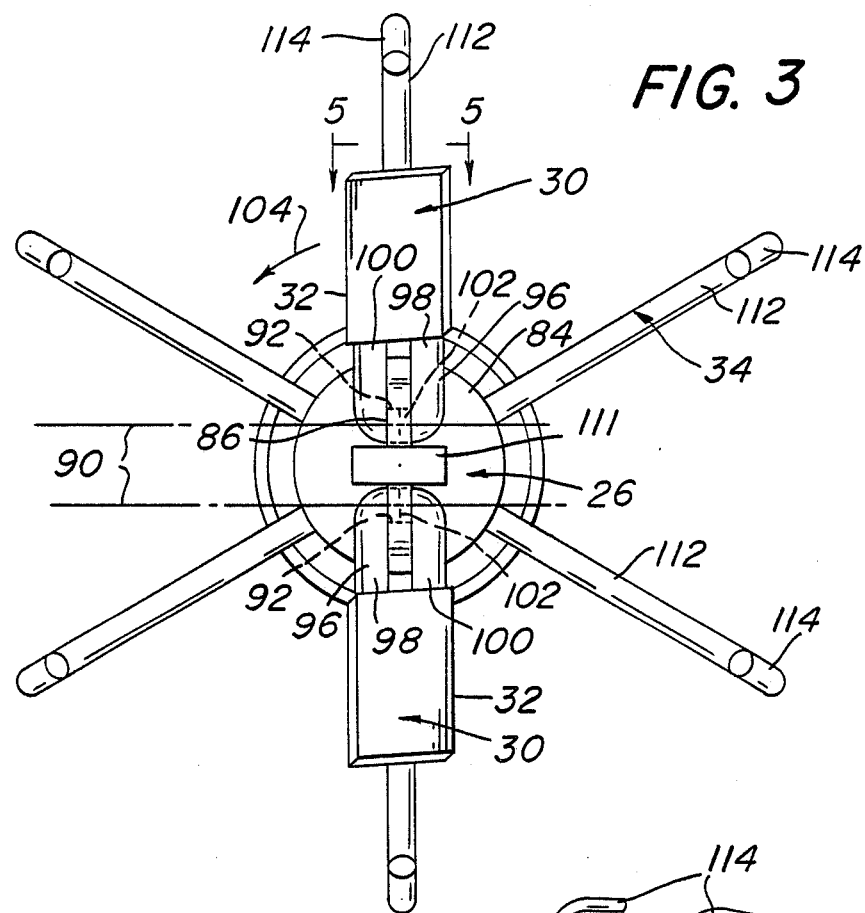
FIG. 3
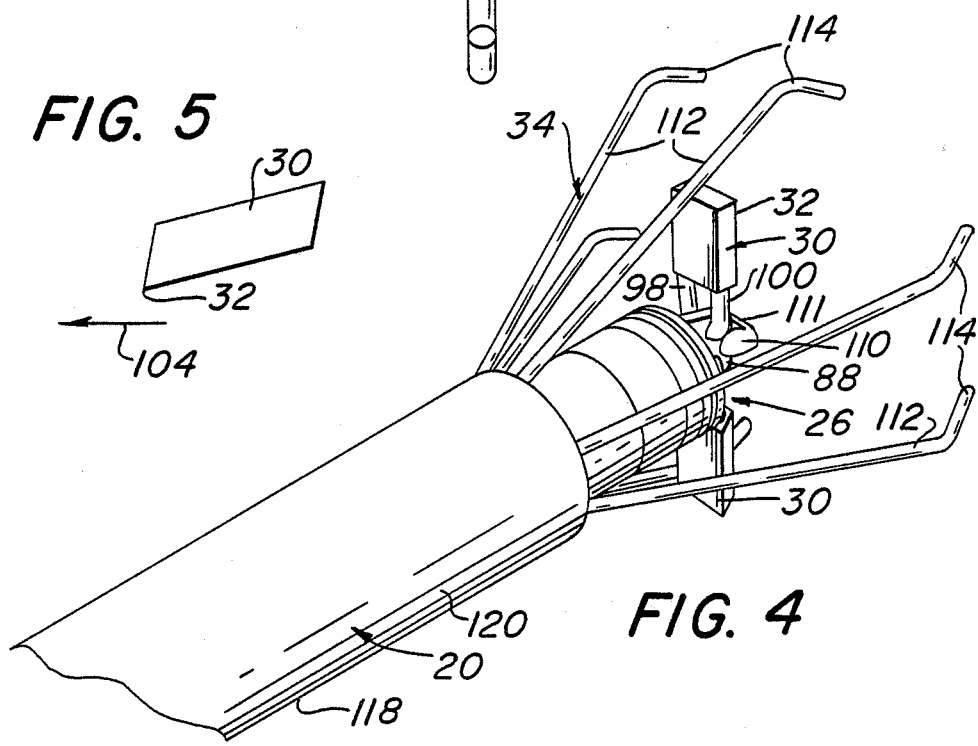
FIG. 5
FIG. 4

STONE DESTROYING CATHETER AND METHOD OF USE

BACKGROUND OF THE INVENTION

This invention relates generally to medical devices and more particularly to flexible, power-driven catheters for destroying stones or other hard bodies located within the body of a living being.

In U.S. Pat. No. 4,679,558 entitled "Catheter Based Surgical Methods and Apparatus Therefor", assigned to the same assignee as this invention, there is disclosed and claimed a catheter for effecting the destruction of a stone or other hard body, e.g., a body containing calcium, located within a living being.

While the catheter disclosed in that application is suitable for its intended purposes to disintegrate or otherwise destroy some stones or other hard bodies, it may nevertheless leave something to be desired from the standpoint of destroying stones which are not held within a duct or lumen in the body.

OBJECTS OF THE INVENTION

Accordingly, it is a general object of the instant invention to provide apparatus for effecting the disintegration or destruction of a stone within the body of a living being which overcomes the disadvantages of the prior art.

It is a further object of this invention to provide apparatus for quickly disintegrating or otherwise destroying a stone within the body of a living being.

It is still a further object of this invention to provide apparatus for disintegrating or otherwise destroying a stone within the body of a living being and for protecting the surrounding tissue from damage or injury during the stone destruction procedure.

It is yet a further object of the instant invention to provide apparatus for disintegrating or otherwise destroying a stone which may be located within a portion of the bodies so that the stone is unconstrained and free to move about.

SUMMARY OF THE INVENTION

These and other objects of the instant invention are achieved by providing apparatus for disintegrating or otherwise destroying a stone within the body of a living being. The apparatus comprises a small diameter instrument having an elongated portion including a longitudinal axis and comprising a working head. The elongated portion is capable of being located at a position within the body so that the working head is adjacent the stone. The working head is arranged to be rotated at a high speed about the axis. The working head comprises at least one impacting member having an impacting surface. The impacting member is arranged to move from a retracted position, wherein the impacting surface is located adjacent the periphery of the elongated portion of the apparatus, to an extended position, wherein the impacting surface extends substantially beyond the periphery of the elongated portion of the apparatus when the working head is rotated. Each impacting surface is arranged when rotated about the axis in the extended position to impact the stone to disintegrate or otherwise destroy the stone.

DESCRIPTION OF THE DRAWING

Other objects and many of the attendant advantages of the instant invention will be readily appreciated when the same becomes better understood by reference to the following detailed description when considered in connection with the accompanying drawing wherein:

FIG. 3 is an end elevational view of a catheter in its operative state;

FIG. 4 is a reduced size perspective view of the distal portion of the catheter in its operative state;

FIG. 5 is an enlarged sectional view taken along line 5—5 of FIG. 3; and

FIG. 6 is an illustration of the catheter of the subject invention shown in its operative state with a gall bladder for effecting the destruction of stones therein.

DETAILED DESCRIPTION OF THE PREFERRED EMBODIMENT

Figure 1:
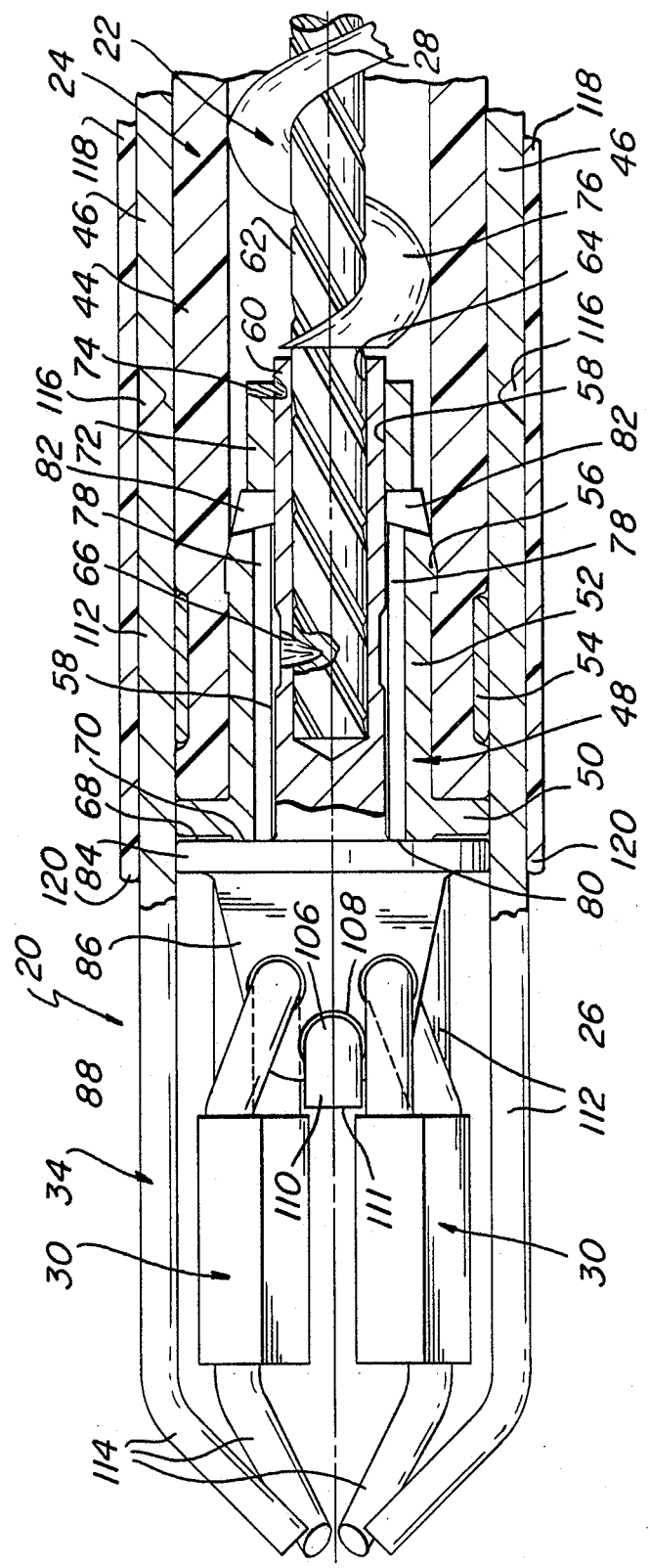
FIG. 1 is a side elevational view, partially in section, showing the distal end of a catheter for pulverizing or otherwise destroying a stone within the body of a living being, with said catheter shown in its compact or inoperative state suitable for introduction to the situs of the stone.

Referring now in greater detail to the various figures of the drawing wherein like reference characters refer to like parts, there is shown at 20 in FIG. 1 a distal end of a catheter for disintegrating or otherwise destroying a stone or other loose body located within the body of a living being. The catheter 20 includes a flexible drive assembly 22 constructed in accordance with the teachings of U.S. patent application Ser. No. 746,220, filed on June 19, 1985, entitled "Spiral Wire Bearing For Rotating Wire Drive Catheter", and U.S. patent application Ser. No. 938,698 filed on Dec. 5, 1986, entitled "Catheter With Means To Prevent Wear Debris From Exiting", which applications are assigned to the same assignee as this invention, and whose disclosures are incorporated by reference herein.

The drive assembly 22 is disposed within a very small diameter, elongated, flexible tubular member 24 having a distal end at which a working head 26 is mounted for high speed rotation about the longitudinal axis 28 of the catheter. The proximal end portion (not shown) of the catheter is adapted to be connected to a source of rotary power, e.g., an electric motor (not shown). The drive assembly 22, extends the length of the catheter to drive, e.g., rotate, the working head 26 under power provided from the remote power source (motor).

The working head will be described in considerable detail later. Suffice for now to state that the working head includes at least one blade 30 which is arranged to be extended from a retracted position wherein it lies close to axis 28 to an extended position like that shown in FIG. 2 wherein it extends substantially beyond the periphery of the catheter. The blade includes at least one impacting surface 32, also to be described later, which is arranged to impact a stone 36 (FIG. 2) or other hard, loose body when the working head is rotated to pulverize, disintegrate or otherwise destroy the stone.

In the preferred embodiment the working head comprises at least two blades. Moreover the blades are arranged in a screw pitch so that when the working head is rotated they produce a powerful vortex flow in the surrounding fluid which serves to draw the stones into the blades. In order to guide the stones toward (into) the rotating blades, while also protecting the surrounding body tissue from being damaged by the rotating blades, the catheter 20 also includes shroud/guide means 34 located adjacent the working head 26.

The shroud/guide means 34 will also be described in detail later. Suffice for now to state that such means is expandable from a compact state, like shown in FIG. 1, to an expanded state, like shown in FIG. 2. When in the compact state the shroud/guide is of an outside diameter no greater than that of the catheter 20 to facilitate the placement of the catheter at the situs of the stone to be destroyed. In the preferred embodiment embodiment of the device shown herein, the outside diameter of the catheter is approximately 1.65 mm (5 French).

The catheter 20 is particularly suited for destroying gallstones within the gall bladder with minimum invasion of the patient's body. As is known, gallstones are loose hard bodies located within the gall bladder 38, an extremely fragile, hollow structure like that shown in the illustration of FIG. 6. The catheter 20 is arranged to be introduced while in its compact, blade-retracted state percutaneously and threaded through the patient's liver (not shown) and through a small opening or puncture 38 in the gall bladder so that the working head extends into the liquid 42 therein. The shroud/guide means 34 is arranged to be moved to the extended state (as will be described later) once the working head 26 of the catheter is in position within the liquid in the interior of the gall bladder. The catheter is then operated, that is the motor started so that the working head commences rotation at a high rate of speed, e.g., from 5,000 to 100,000 rpm. This action causes the blades to move to the extended position of FIG. 2.

As noted earlier when the shroud/guide means 34 is in the expanded position it serves to protect the fragile wall of the gall bladder from the rotating blades. In addition, the shape of the shroud/guide means 34 serves to direct the stones toward the rotating blades in cooperation with the vortex produced by the rotation of the blades in the liquid 42. Large stones (like that shown in FIG. 2) which cannot fit fully into the interior of the shroud/guide means are nevertheless held within its open mouth so that the portion of the stone extending therein can be impacted by the rotating blades. This action reduces the size of the large stone, so that it can pass through the mouth fully into the blades, whereupon it is ultimately disintegrated or destroyed.

While the device of this invention may not require the expanding blades for some applications, the use of expanding blades is preferred to enable the catheter to produce a more powerful vortex than would be otherwise possible with blades of a fixed size yet sufficiently small to enable the catheter to be readily inserted into and threaded through the body to the situs of the stone.

As will be appreciated by those skilled in the art from the description to follow, the vortex created within the gall bladder recirculates the liquid 42 and the stones 34 into the rotating blades 30 so that their impacting surfaces 32 can repeatedly impact the stones to progressively reduce the size of the stones by pulverization or fragmentation.

In order to expedite the destruction of the stones, the catheter 20 can be utilized in conjunction with a suitable stone dissolving solvent. Such a technique may effect a more rapid disintegration of the stones as a result of the violent agitation and impaction caused by the blades, than could be otherwise achieved by the introduction of a solvent alone. Thus, in accordance with one aspect of this invention the central passageway down the catheter can be used to carry any suitable solvent for aiding in the destruction of the stone into the gall bladder. After running the catheter 20 for a predetermined period of time, e.g., ten minutes, the fluid 42 and pulverized material produced during the stone disintegration process can be extracted or sucked out of the bladder through the catheter and fresh solvent thereafter introduced therethrough. This procedure is then repeated until all of the stones are disintegrated or destroyed. The use of the shroud/guide means 34 by protecting the delicate wall of the gall bladder 38 enables the catheter 20 to be left operating in place for a sufficiently long period of time, e.g., one hour or more, to ensure that all of the stones 36 are destroyed or reduced to an acceptable size.

Figure 2:
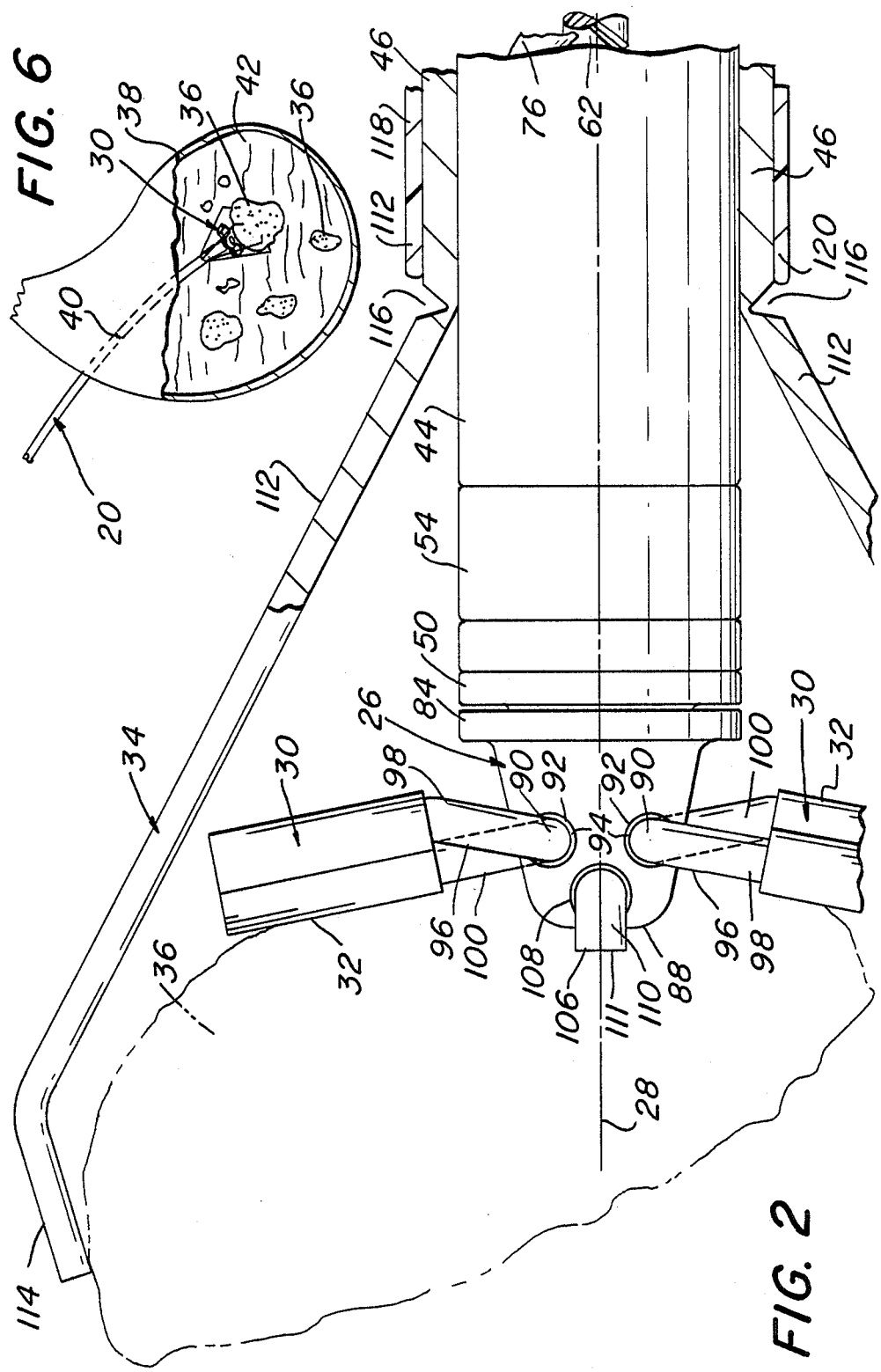
FIG. 2 is a side elevational view, partially in section, of the catheter shown in FIG. 1 but shown in the expanded or operative state for effecting a stone destruction operation.

Referring to FIGS. 1 and 2, the details of the distal end of a preferred embodiment of the catheter 20 will now be described. As can be seen the catheter 20 basically comprises an elongated, flexible tubular member or jacket 44 which is formed of a suitable material, e.g., plastic, and which has a small outside diameter. Disposed about the tubular jacket 44 is a sleeve 46 extending substantially the entire length of the catheter and whose distal end forms the shroud/guide means 34. In a preferred embodiment shown herein the outside diameter of the jacket is approximately 1.7 mm (5 French) or less. The wall of the sleeve 46 is quite thin, e.g., 0.15 mm, so that the outside diameter of the catheter 20 is approximately 6 French (2 mm). This size catheter is merely exemplary. Thus, in accordance with this invention, the catheter can be constructed as small and as large as necessary.

At the distal end of the catheter 20 there is secured a sleeve-like bushing 48. The bushing includes a flanged end face 50 arranged to abut the end of the catheter's jacket 44 and a tubular portion 52. The outside diameter of tubular portion 52 is approximately that of the inside diameter of the catheter's jacket 44 so that it is snugly fit therein. The bushing is held firmly in place by a retaining band 54 which tightly encircles the periphery of the catheter jacket 44 so that plural gripping teeth 56 located about the periphery of the tubular portion 52 dig into the interior surface of the catheter jacket 44 and hold the bushing tightly in place therein. The bushing 48 also includes a bore 58 extending therethrough and aligned with the longitudinal central axis 28 of the catheter.

The working head 26 includes a mounting shank or axle 60 projecting proximally and passing through the bore 58 in the bushing 48. A multistrand drive cable 62 extends down the catheter's jacket 44 coaxial with axis 28 and terminates and is disposed within a longitudinal extending bore 64 in the shank 60 of the working head 26. The end of the drive cable 62 is secured in place in the bore 64 via a laser weld joint 66. The shape of the working head 26 and its various components will be described later. Suffice now to state that it includes a generally planar rear surface 68 which lies closely adjacent to and engages the front surface 70 of the bushing's flange 50. The working head 26 is prevented from axial movement within the bushing 48 by virtue of a retaining ring 72 mounted on the proximal end of the working head axle 60 contiguous with the proximal end of the bushing. The retaining ring 72 is secured to the proximal end of the working head axle 60 via another laser weld 74.

The drive cable 62 is supported in the central position along axis 28 by means of a spiral bearing 76. That bearing member 76 thus comprises a helical or spiral cylindrical coil of wire surrounding the multistrand drive cable 62. The spiral bearing extends substantially the entire length of the catheter from a proximately located point adjacent the drive motor (not shown) to the distal end of the catheter. The outer diameter of the helical bearing coil is sufficiently great so that its loops just clear the interior surface of the catheter's jacket 44 to hold the bearing securely in place therein. The inside diameter of the central passageway extending down the length of the helical bearing is just slightly greater than the outside diameter of the drive cable 62 so that the drive cable can freely rotate about axis 28 therein.

It should be pointed out at this juncture that the drive cable 48 can, if desired, be drawn or swaged so that its outer periphery of the cable has a greater contact surface area with the spiral bearing than if the cable were unswaged. This feature is shown and claimed in the aforementioned copending U.S. patent application Ser. No. 938,698. Also disclosed and claimed in that application is a spiral bearing wire whose inner surface, that is, the surface defining the central passageway therethrough, is substantially planar in order to further increase the engaging surface areas. A bearing constructed in accordance with that feature can, if desired, be used to support the drive cable 62 herein.

With such a construction, the drive cable 62 can be rotated at a high rate of speed, e.g., up to 100,000 rpm, while the catheter is bent through a small radius of curvature, e.g., 0.75 inches (1.9 cm), and without the creation of any standing waves which could result in unwanted vibration to the catheter.

The spacing between the convolutions of the spiral bearing, the inner surface of the catheter jacket 44 and the outer surface of the drive cable 62 form a passageway through which a fluid (e.g., a liquid) can flow from the proximal end of the catheter to the distal end. This fluid can be utilized to cool or lubricate the bearing system. Moreover, the liquid which is passed down the catheter can, as noted earlier and if desired, be a solvent to aid in the stone destruction process. Also, if desired, nitrates, contrast media or other drugs can be added to the liquid as needed during the procedure.

The means for enabling the fluid (e.g., liquid) to exit the catheter adjacent the distal end of the catheter can comprise one or more apertures (not shown) in the wall of the jacket immediately proximally of bearing 48 and which communicate with the central passageway in the catheter and/or four, equidistantly spaced, grooves 78 (FIG. 1) extending longitudinally down the central bore 58 of the bearing 48 and also communicating with the central passageway. The distal end of each groove 78 terminates at a fluid exit port 80 located at the distal end flange 50 of the bushing, while the proximal end of each groove 78 terminates in a respective, generally radially extending, relief groove 82. A fluid passing down the interior of catheter jacket flows under pressure into the relief grooves 82, through the associated longitudinal grooves 78 out through the ports 80 at the end face of the catheter and into the interface space (not shown) between the proximal end of the working head and the front face 70 of the flange 50. Thus, the fluid gains egress from the catheter.

The details of the working head 26 and its components will now be discussed. The working head 26 is arranged to rotate about the axis 28. As can be seen the working head basically comprises a base portion 84 in the form of a circular disk and from which a support hub 86 projects. The support hub basically comprise a generally thin projection centered along the axis of rotation 28 and terminating at a free end portion 88. Each of the blades 30 is a generally planar, elongated member having an elongated side edge forming the heretofore identified impacting surface 32. Each blade is pivotably secured to the support hub 86 to enable the blade to pivot about a respective transverse axis 90 (FIG. 3) extending perpendicularly to the axis of rotation and parallel to the sides of the hub. Thus, the hub 86 includes a pair of holes 92 extending therethrough, with each hole centered on axis 90. A bearing sleeve 94 may be located within each hole. Each blade 30 is mounted on the hub, via a respective support frame 96. Each frame 96 is a generally U-shaped member having a pair of side legs 98 and 100 and an intermediate axle portion 102. The axle portion 102 of each frame is journalled in a respective bearing sleeve 94 and with its associated legs 98 and 100 extending on either side of the hub. Each leg of each frame is fixedly secured to the blade so that the blade extends outward from its support legs. The two legs of each frame are twisted with respect to each other about axis 90 so that each blade 30 is twisted with respect to the other to form a screw pitch. In particular the blades are twisted so that the impacting surface side edge is the leading edge of the blade as the head rotates about axis of rotation 28. Moreover, the impacting surface 32 of each blade 30 is disposed generally distally of the trailing edge of the blade. This is clearly shown in FIG. 5 wherein the pitch of the upper of the two blades 30 shown in FIG. 3 is shown with respect to an arrow 104 representing the direction of rotation of the working head 26 about axis of rotation 28.

When the blades 30 are in the retracted position they lie generally along respective axes extending generally parallel to the axis of rotation 28 or at a slight outward angle with respect thereto. As the working head rotates the centrifugal force on the blades causes the blades to pivot outward about the respective transverse axes 90 to the extended position shown in FIG. 2, whereupon the blades extend up to a maximum angle, e.g., 90°, with respect to the axis of rotation. With the blades in this orientation and rotating about axis 28 their screw pitch produces a powerful vortex which is directed generally inward toward the center of the working head. This vortex recirculates the liquid and stones into the rotating blades to effect the progressive size reduction (destruction) thereof. As will be appreciated by those skilled in the art, if the blades were of a fixed size so that they did not extend substantially beyond the outside diameter of the catheter they would tend to bore a hole in large stones rather than to fragment them. By having the blades pivot outward to a position substantially beyond the outer diameter of the catheter itself one can create a very powerful vortex (the power in a vortex is proportional to the blade diameter to the fifth power). It is also contemplated that the blades may be weighed at their free ends or otherwise constructed to include heavy tips providing a large mass at the radially outward position, thereby providing higher kinetic energy to aid in the stone destruction process.

In order to insure that the blades pivot outward upon rotation of the working head it is important that the blades start from a retracted position in which they are separated slightly from each other. Accordingly stop means 106 is provided on the hub to start the blades from an appropriate orientation. The stop means is mounted in a hole 108 in the hub adjacent the free end thereof and located between the two transverse holes 92. The stop means basically comprises a pair of short length side legs 110 which lie on each side of the hub adjacent the axis 28 and which are bridged by a section 111 at the distal ends thereof. The other end of each leg extends into the hole 108. The section 111 being interposed between the blades thus prevents the blades from touching each other or extending inward toward the axis of rotation, either of which action may prevent the blades from pivoting outward when the working head is rotated.

The details of the shroud/guide means 34 will now be considered. To that end that means basically comprises a plurality of equidistantly spaced prongs 112, each of which is an extension of the sleeve 46. Each prong is an elongated member having a free end portion 114 bent at an acute angle to the remaining portion of the prong. Each prong merges with the sleeve 46 at a living or flex hinge 116. Each hinge is formed so that the associated prong is normally biased outward to the extended position shown in FIGS. 2-4. In order to retract the prongs to the retracted position of FIG. 1, the catheter 20 includes a tubular compressor sleeve 118. This compressor sleeve can serve as the means for introducing the catheter into the body of the patient. The inside diameter of the compressor sleeve 118 is just slightly larger than the outside diameter of the sleeve 46 to enable the sleeve 118 to be slid longitudinally with respect to the sleeve 46. When the free end 120 of the compressor sleeve 118 is located so that it extends over the prongs 112, the hinges 116 are flexed against their natural bias to force the prongs into the retracted position shown in FIG. 1. In this position the catheter 20 can be readily introduced to the situs of the stones to be destroyed. Once the distal end of the catheter is at the desired location the compressor sleeve 118 is withdrawn, that is slid proximally with respect to the catheter so that its free end 120 is located proximally with respect to the hinge 116. Accordingly the natural bias of the hinges 116 causes the prongs 112 to flex outward to the position shown in FIGS. 2-4. The catheter is now ready for operation by the rotation of the working head 26 about the axis of rotation, as described heretofore.

It has been found that in some applications it may be desirable to periodically rotate the working head in the opposite direction as the normal direction (e.g., the direction of arrow 104 in FIG. 5) in order to clear the working head of any entrapped stones or fragments. Hence the drive system is arranged to rotate the working head in either direction upon command.

The working head may also include at least one aperture to the exterior thereof and in fluid communication with the interior of the catheter. This aperture, can also provide a means for introducing a solvent or other liquid into the body at the situs of the stone to be destroyed, while also serving as a passageway through which the stone fragments can be extracted by suction through the catheter.

It should also be noted that while the catheter and its method of use as described heretofore has focused on the destruction of gall stones, it should be clear that the subject catheter can be utilized to destroy any type of stone located within the body of a living being, and whether the stone is free floating (that is, located loosely within a body organ or tissue), or closely confined (that is, constrained or held within some body portion, e.g., a duct, etc.). In the former case the use of the vortex is of considerable importance whereas in the latter case it is of less importance.

In accordance with the preferred embodiment of the invention the working head, and in particular its blades, is formed of a tough and impact resistant material, such as a suitable metal, alloy, plastic, etc. The shroud and its extension sleeve may be formed of any suitable flexible, resilient material such as plastic.

Without further elaboration the foregoing will so fully illustrate my invention that others may, by applying current or future knowledge, adopt the same for use under various conditions of service.

What is claimed is:

1. Apparatus for disintegrating or otherwise destroying a stone within the body of a living being, said apparatus comprising a small diameter instrument having an elongated portion including a longitudinal axis and comprising a working head, said elongated portion capable of being located at a position within said body wherein said working head is adjacent the stone, said working head being coupled to means for rotating said working head at a high speed about said axis, said working head comprising a first portion, at least one impacting member having an impacting surface thereon, and coupling means movably coupling said impacting member to said first portion for enabling said impacting member to move from a retracted position to an extended position, said impacting surface being located a greater radial distance from the longitudinal axis of the elongated portion of the apparatus when in said extended position than when in said retracted position, said impacting surface being arranged when rotating in said extended position to impact said stone to disintegrate or otherwise destroy it.

2. The apparatus of claim 1 additionally comprising means for directing said stone to said rotating impacting member.

3. The apparatus of claim 2 wherein said directing means comprises a shroud located adjacent said working head.

4. The apparatus of claim 3 wherein said shroud has an open distal end and is flared outward from a point closely adjacent said working head to said distal end, said distal end of said shroud defining an enlarged mouth into which at least a portion of said stone can enter.

5. The apparatus of claim 4 wherein said shroud is expandable from a retracted position to an expanded position wherein said shroud is flared outward to define said enlarged mouth.

6. The apparatus of claim 5 wherein said shroud comprises a plurality of elongated ribs.

7. The apparatus of claim 4 wherein said shroud comprises a plurality of elongated ribs.

8. The apparatus of claim 1 additionally comprising means for protecting adjacent body tissue from being engaged by said impacting member as it rotates.

9. The apparatus of claim 8 wherein said protecting means comprises a shroud located adjacent said working head.

10. The apparatus of claim 9 wherein said shroud has an open distal end and is flared outward from a point closely adjacent said working head to said distal end, said distal end of said shroud defining an enlarged mouth into which at least a portion of said stone can enter.

11. The apparatus of claim 10 wherein said shroud is expandable from a retracted position to an expanded position wherein said shroud is flared outward to define said enlarged mouth.

12. The apparatus of claim 11 wherein said shroud comprises a plurality of elongated ribs.

13. The apparatus of claim 10 wherein said shroud comprises a plurality of elongated ribs.

14. The apparatus of claim 1 wherein said working head comprises a pair of impacting members, said impacting members being disposed diametrically opposite each other with respect to said axis.

15. The apparatus of claim 14 wherein each of said impacting members comprises a blade.

16. The apparatus of claim 15 wherein each of said blades is disposed at an angle so that upon the rotation of said working head said blades create a vortex tending to pull said stone into said blades.

17. The apparatus of claim 16 wherein each of said blades is connected to said coupling means and is arranged to pivot with respect to a respective axis each oriented transverse to said longitudinal axis to enable each of said blades to pivot from said retracted position to said extended position.

18. The apparatus of claim 17 additionally comprising stop means located between said blades to hold said blades apart when said blades are in said retracted position.

19. The apparatus of claim 16 additionally comprising means to direct said stone to said blades.

20. The apparatus of claim 19 wherein said directing means comprises a shroud located adjacent said working head.

21. The apparatus of claim 20 wherein said shroud has an open distal end and is flared outward from a point closely adjacent said working head to said distal end, said distal end of said shroud defining an enlarged mouth into which at least a portion of said stone can enter.

22. The apparatus of claim 16 additionally comprising means to protect adjacent body tissue from being engaged by said blades.

23. The apparatus of claim 22 wherein said protecting means comprises a shroud located adjacent said working head.

24. The apparatus of claim 23 wherein said shroud has an open distal end and is flared outward from a point closely adjacent said working head to said distal end, said distal end of said shroud defining an enlarged mouth into which at least a portion of said stone can enter.

25. The apparatus of claim 1 wherein said coupling means for enabling said impacting member to move from said retracted position to said extended position comprises means for enabling said movement when said working head is rotated.

26. The apparatus of claim 25 wherein said working head comprises a pair of impacting members, said impacting members being disposed diametrically opposite each other with respect to said axis.

27. The apparatus of claim 26 wherein each of said impacting members comprises a blade:

28. The apparatus of claim 27 wherein each of said blades is disposed at an angle so that upon the rotation of said working head said blades create a vortex tending to pull said stone into said blades.

29. The apparatus of claim 28 wherein each of said blades is connected to said coupling means and is arranged to pivot with respect to a respective axis each oriented transverse to said longitudinal axis to enable each of said blades to pivot from said retracted position to said extended position upon the rotation of said working head about said axis.

30. A method for disintegrating or otherwise destroying a stone within the body of a living being by the use of a small diameter instrument, said instrument comprising an elongated portion having a longitudinal axis and a working head, said working head being arranged to be rotated at a high speed about said axis and comprising at least one impacting member having an impacting surface thereon, said method comprising the steps of introducing said instrument into the body of a living being so that said working head is located adjacent said stone, causing said impacting member to move from a retracted position to an extended position, said impacting surface being located a greater radial distance from the longitudinal axis of the elongated portion of the instrument when in said extended position than when in said retracted position, causing the rotation of said working head, whereupon said impacting surface when rotating in said extended position impacts said stone to disintegrate or otherwise destroy it.

31. The method of claim 30 wherein said rotation of said impacting member creates a vortex tending to pull said stone into engagement with said impacting member.

32. The method of claim 30 additional comprising the step of introducing means adjacent said working head to protect adjacent body tissue from being engaged by said impacting member as it rotates.

33. The method of claim 30 additionally comprising the step of introducing means adjacent said working head to direct said stone to said rotating impacting member.

* * * * *